United States Patent [19]
Allan

[11] Patent Number: 5,518,003
[45] Date of Patent: May 21, 1996

[54] MID-STREAM FLUID SAMPLER

[75] Inventor: John R. Allan, Whitby, Canada

[73] Assignee: Durimport Maine Limited, Ontario, Canada

[21] Appl. No.: 158,890

[22] Filed: Nov. 30, 1993

[51] Int. Cl.$^6$ ................................................ A61M 1/00
[52] U.S. Cl. ........................ 128/761; 128/760; 604/317
[58] Field of Search ................................. 128/760, 761, 128/762, 317, 322

[56] References Cited

U.S. PATENT DOCUMENTS

| | | | |
|---|---|---|---|
| 3,345,980 | 10/1967 | Coanda | 128/762 |
| 3,499,327 | 3/1970 | Lane, Jr. . | |
| 3,625,064 | 12/1971 | Hinman, Jr. et al. . | |
| 3,625,654 | 12/1971 | Van Duyne | 128/760 |
| 3,635,091 | 1/1972 | Linzer et al. . | |
| 3,830,107 | 8/1974 | Linzel et al. | 128/701 X |
| 3,832,738 | 9/1974 | Klieman et al. | 128/761 X |
| 4,040,791 | 8/1977 | Kuntz . | |
| 4,252,132 | 2/1981 | Kuntz . | |
| 4,301,812 | 11/1981 | Layton et al. . | |
| 4,494,581 | 1/1985 | Gordon . | |
| 5,092,859 | 3/1992 | Everett et al. | 128/760 X |

FOREIGN PATENT DOCUMENTS 0373917  8/1990  European Pat. Off. .

*Primary Examiner*—Sam Rimell
*Attorney, Agent, or Firm*—Lowe, Price, LeBlanc & Becker

[57] ABSTRACT

A fluid sampling device which collects the initial sample of a fluid stream, discards it and collects a mid-stream sample for future analysis. When used for the collection of urine, the initial sample is collected in a hopper, which after collecting the initial sample, rotates from a first position to a second position and discards some of the initial sample. While in its second position, a surface of the hopper diverts the mid-stream sample to the container for collection of the sample.

36 Claims, 4 Drawing Sheets

MID-STREAM FLUID SAMPLER

BACKGROUND AND SUMMARY OF THE INVENTION

The present invention relates to a fluid sampling device, more particularly a urine collector for automatically collecting a mid-stream sample of urine while the patient urinates normally.

Urine, a bodily fluid, contains chemicals and metabolites indicative of certain physiological processes or disorders. In order to properly analyze the urine, a sample must be collected which is relatively free of contaminants. Contaminants are entrained into the initial portion of urine stream as the urine passes through the urethra and, in the case of Women, the vaginal walls. Accordingly, it is preferable to collect a sample of urine in mid-stream.

Currently, a mid-stream sample of urine is collected by the patient urinating for a few seconds, stopping urination and then urinating into a sample vial. The procedure can be messy and, in the case of persons having difficulty with sphincter control, next to impossible.

Other devices have been developed for the collection of a mid-stream sample of urine. For example, U.S. Pat. No. 3,830,107 discloses a disposable urine specimen collector which is provided with a flexible inner enclosure to collect the initial specimen. Upon collecting the desired amount, the flexible bag disengages from the inlet of the device and permits the urine specimen to be collected in the outer enclosure. The device is made of a variety of materials and retains the initial urine sample making disposal or recycling difficult.

U.S. Pat. No. 3,499,327 provides for a urine collector having a diverting valve which redirects the flow of urine through the device so as to segregate the initial stream sample from the mid-stream sample. A disadvantage of the device is that all the urine flows over a surface in the inlet region thus exposing it to contamination by the initial stream of urine.

In general terms, this invention provides a mid-stream fluid sample collection device comprising a housing to receive the stream of fluid and a hopper which first collects and then discards some of the initial sample of fluid and then diverts the mid-stream sample to a sample container.

More particularly, the invention provides a fluid sample collection device comprising a housing having an inlet to receive a stream of fluid and a container to retain a mid-stream fluid sample, a hopper movably associated within the housing and positioned to receive and retain fluid flowing through said inlet, said hopper being adapted to move from an initial first position in which said hopper collects a predetermined volume of the the first portion of the fluid stream and thereby moves to a subsequent second position in which an outer surface of the hopper is impinged by the fluid stream and diverts the mid-stream fluid sample to said container.

In another embodiment, this invention provides a mid-stream urine sample collection device comprising a housing to receive the stream of urine and a hopper which first collects and then discards some of the initial sample of urine and then diverts the mid-stream sample to a sample container.

More particularly, the invention provides a mid-stream urine sample collection device comprising a housing having an inlet to receive a stream of urine and a container to retain a mid-stream urine sample, a hopper movably associated within the housing and positioned to receive and retain urine flowing through said inlet, said hopper being adapted to move from an initial first position in which said hopper collects a predetermined volume of the the first portion of the urine stream and thereby moves to a subsequent second position in which an outer surface of the hopper is impinged by the urine stream and diverts the mid-stream urine sample to said container.

BRIEF DESCRIPTION OF THE DRAWINGS AND THE PREFERRED EMBODIMENT

A detailed description of the preferred embodiment is provided below with reference to the following drawings, in which.

Figure 1:
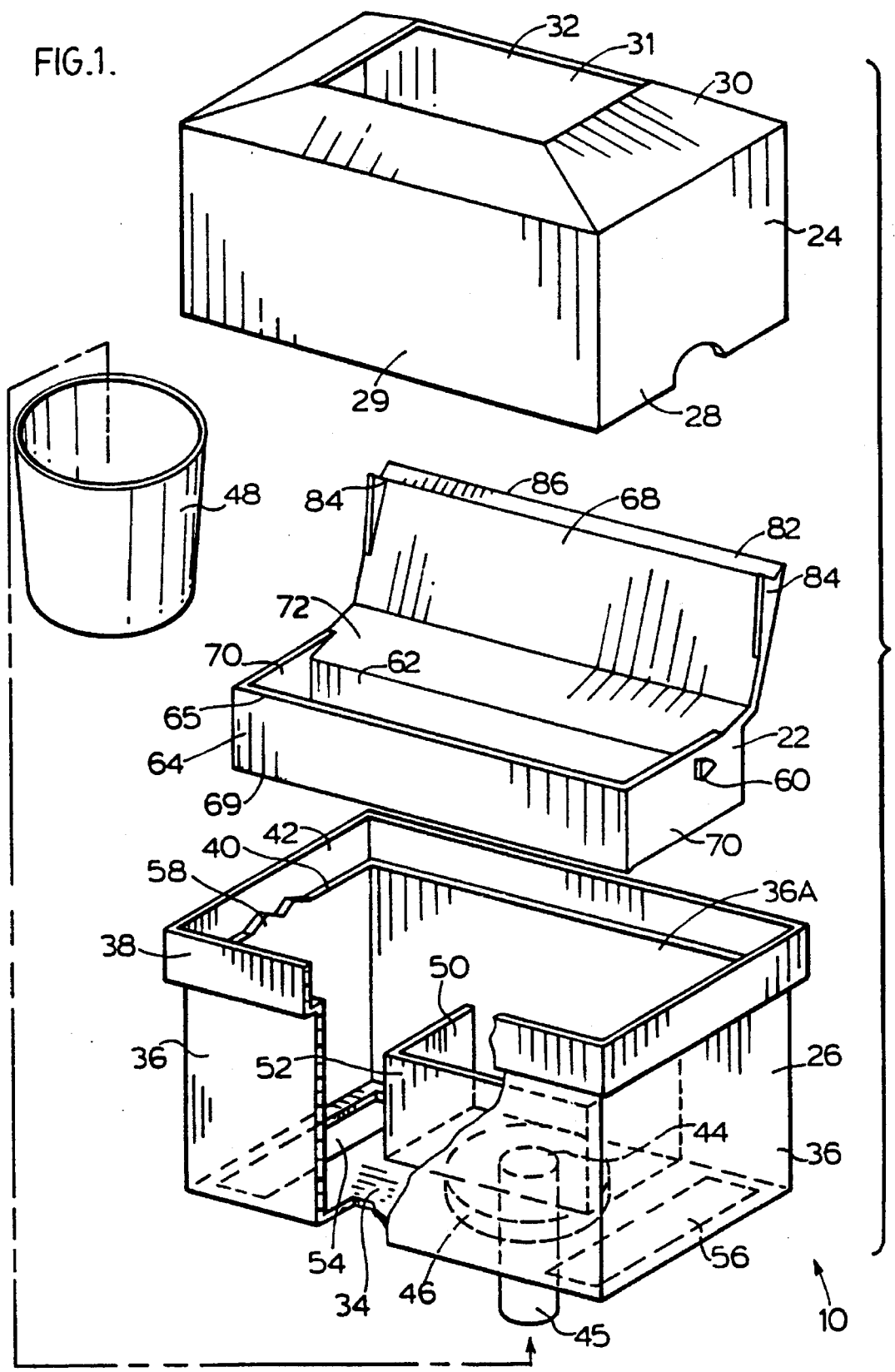
FIG. 1 is an exploded perspective view of the mid-stream sampling device.
Figure 2:
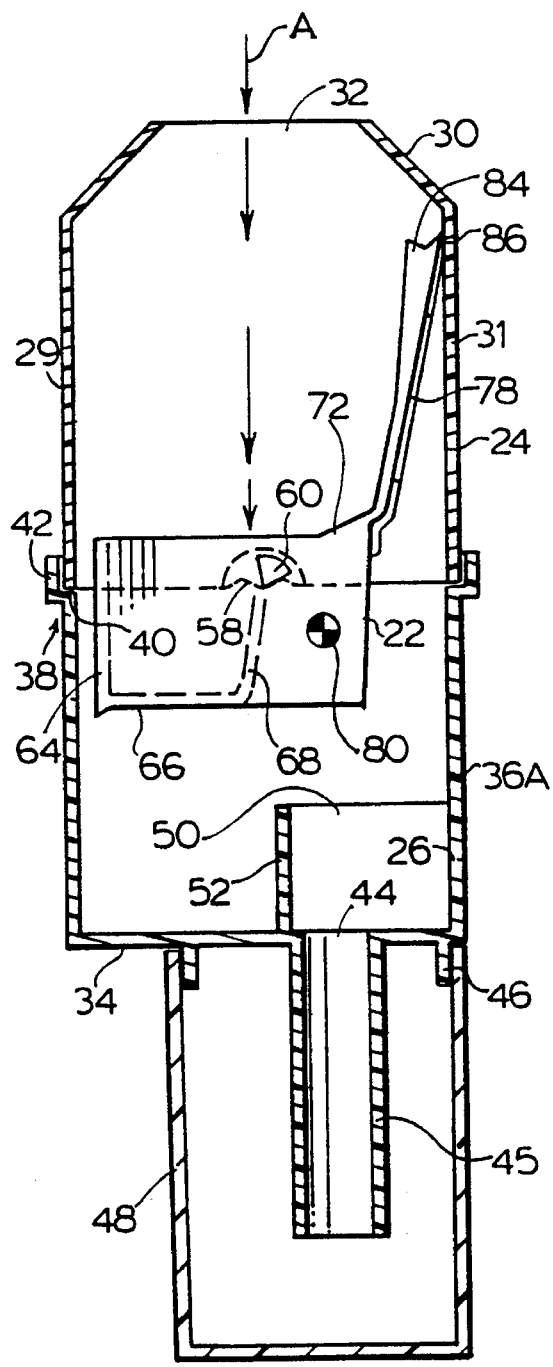
FIG. 2 is a side view partially in section of the hopper in its first position.

With reference to FIGS. 1 and 2, a mid-stream sampling device generally indicated 10 includes a housing 20 and a hopper 22 located within the housing. The housing 20 is formed from a pair of separable portions, namely an upper portion 24 and a lower portion 26.

The upper portion 24 has peripheral walls 28 including front wall 29 and rear wall 31, that are connected to an end wall 30. The end wall 30 slopes upwardly and inwardly from the peripheral walls 28 to define a rectangular opening 32 at the apex of the end wall 30.

The lower portion 26 has a generally rectangular base 34 with walls 36 extending upwardly from the periphery of the base 34. The upper edge of the walls 36, indicated at 38, is formed with a ledge 40 and upstanding flange 42. The ledge 40 supports the upper portion 24 with flange 42 locating the upper portion 24 on the lower portion 26.

The base 34 has a centrally located hole 44 which is offset toward a back wall 36A of the lower portion 26 and has nozzle 45 and cylindrical boss 46 projecting below the base 34. The boss 46 is used to connect a container 48 to the lower portion 26 of the housing 20 and may either have a smooth external surface to provide a friction fit or a threaded external surface to retain the container.

The hole 44 is located within a channel generally indicated at 50 formed by upstanding partitions 52. The partitions 52 are connected to the rear wall 36A to isolate the hole from the balance of the lower portion 26 and terminate below the upper edge of the peripheral walls 36. A pair of apertures 54 and 56 are located to either side of the channel in the base 34 to allow fluid to flow out of the lower portion 26.

The ledge 40 is provided with a pair of notches 58 which act as fulcrum blocks to support knife edges 60 formed on the hopper 22 and allow pivotal movement of the hopper relative to the housing. The hopper 22 is formed as an elongate trough generally indicated at 62 formed from a front wall 64, a base 66 and an elongate rear wall 68. A pair of end walls 70 extend between the front wall, base and rear wall to define the trough 62. The junction between the base 66 and front wall 64 is pointed to define a drip edge 69. The rear wall 68 extends upwardly beyond the front wall 64 and is formed with a ledge 72 to displace an upper portion of the rear wall 68 rearwardly.

The knife edges 60 are integrally formed on the end wall 70 and have a pair of converging flanks 74 to define a pivot axis. An end face 76 of the knife edges 60 slopes outwardly and downwardly relative to the end walls 70 of the trough 62. The end surface intersects with the flanks to define a point 61.

The rear wall 68 extends upwardly from the ledge 72 and has an outer surface 78 directed toward the rear walls 31 of the upper portion 24. A set of vanes 88 are formed on the outer surface 78 and converge downwardly toward the central portion of the outer surface 78. A forwardly facing surface 85 of the rear wall 68 is provided with tabs 84 that extend normal to the surface 85 at opposite ends of it.

The inlet, hopper, holder and container are all preferably made of the same material for easy recycling. The parts are assembled and pre-sterilized and delivered to a customer in a sterilized package.

The principle of operation of the sampler is as follows (with reference to FIGS. 2 and 3). The knife edges 60 of the hopper rest on notches 58 of the lower portion 26 of the housing 10. The hopper 22 freely pivots between a first position (shown in FIG. 2) to second position (shown in FIG. 3). When the hopper 22 is in its first position, its centre of gravity 80 is located between the knife edges 60 and the rear wall 31 of upper portion 24.

The end wall 30 of the upper portion 24 of the housing is, in the case of a female patient, placed against and used to separate the vaginal lips. A male patient simply urinates into the opening 32.

When the patient urinates into the device, urine passes through opening 32 in the upper portion 24 and collects in hopper 22 as indicated by arrow A in FIG. 2. Upper edge 86 of rear wall 68 rests against rear wall 31 of the housing thereby preventing contamination of the rear walls 68 and 31 by the initial stream.

Figure 3:
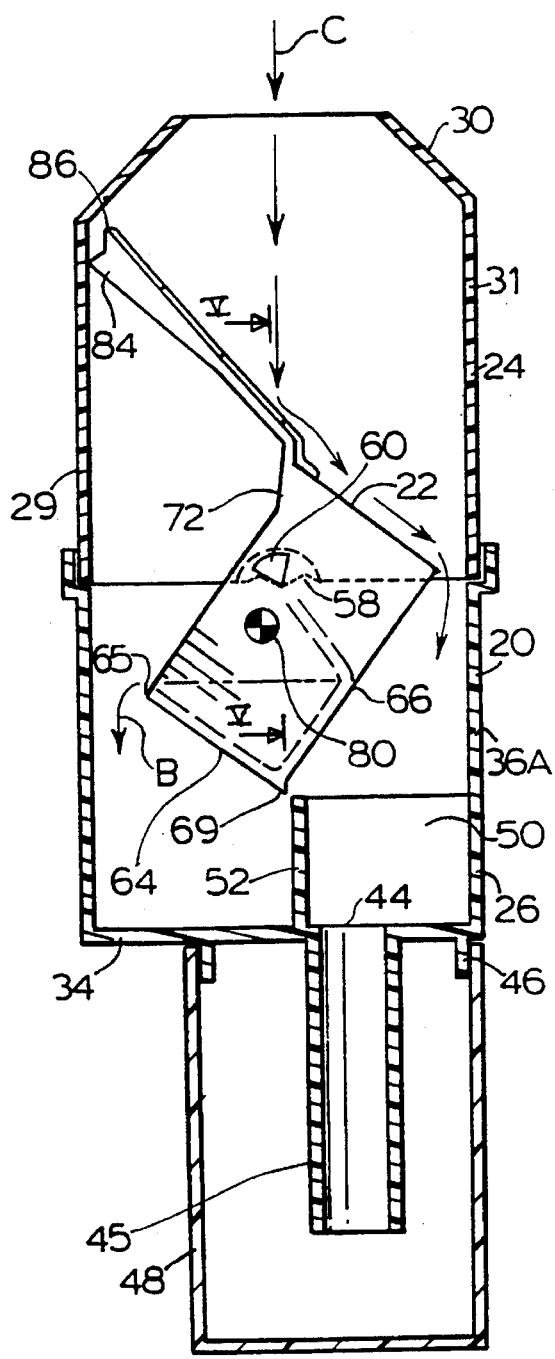
FIG. 3 is a view similar to FIG. 2 of the hopper in its second position.
Figure 4:
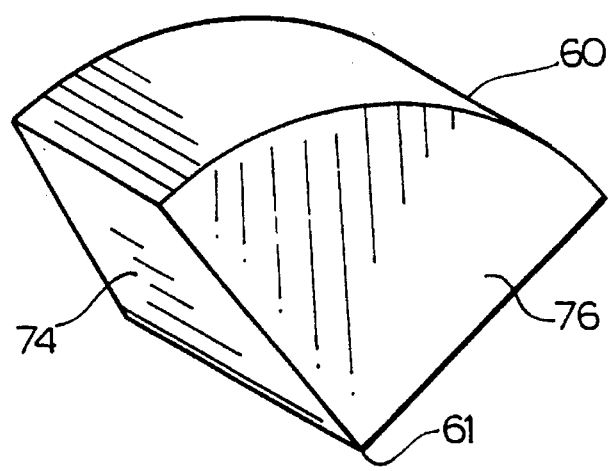
FIG. 4 is a perspective view of a support provided on the hopper.

When the hopper 22 collects a predetermined volume of urine, (approximately 15 to 25 ml) the centre of gravity 80 moves forward of the knife edges 60 and the hopper 22 rotates and tips to its second position as shown in FIG. 4, discharging some of the collected first stream sample of urine into the front of the lower portion 26 of the housing as indicated by arrow B in FIG. 3. This portion of the initial sample of urine exits the lower portion of the housing through apertures 56 and is discarded.

Some of the initial sample remains in the hopper thereby assisting in retaining the hopper in the second position.

The centre of gravity of the hopper in its second position lies between the knife edges 60 and the front wall 29 so that the hopper remains in its second position.

Meanwhile, the patient's urine continues to enter the opening 32. This stream is now the mid-stream of urine which is relatively free of contaminants. The continuing stream of urine is diverted by the outer surface 78 of rear wall 68 of the hopper 22 towards the rear of the lower portion 26 of the housing 20 as shown by arrow C in FIG. 3.

Figure 6:
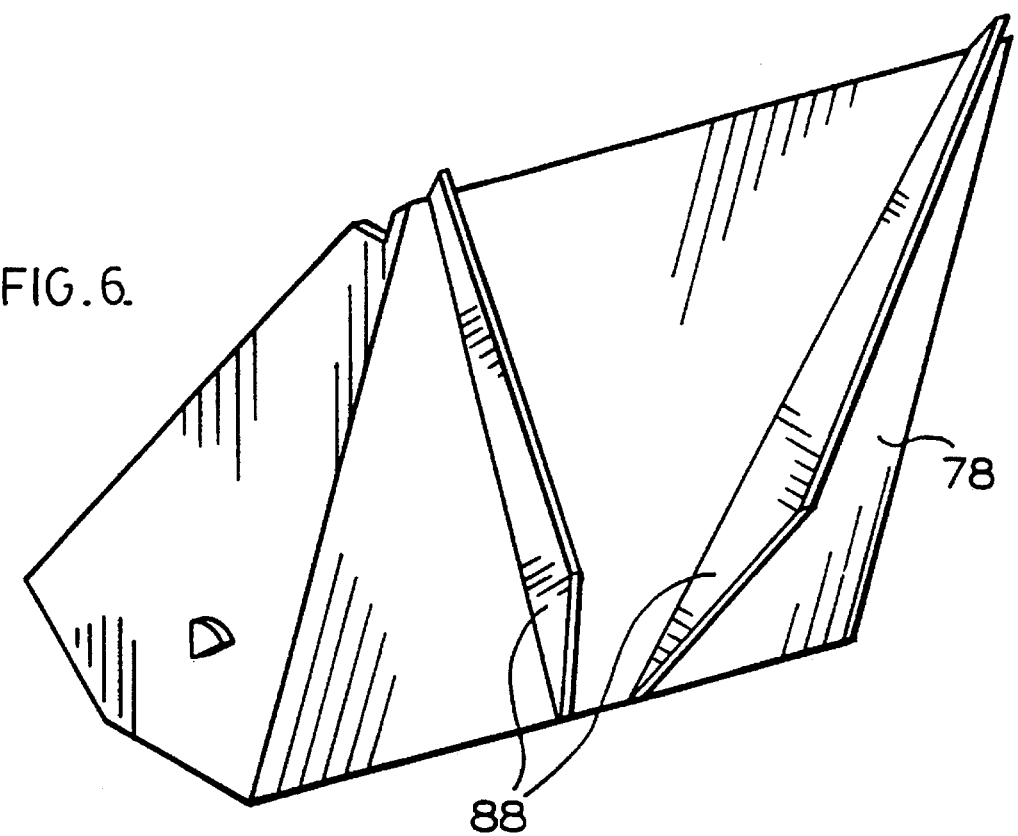
FIG. 6 is a rear perspective view of a first embodiment of hopper.
Figure 7:
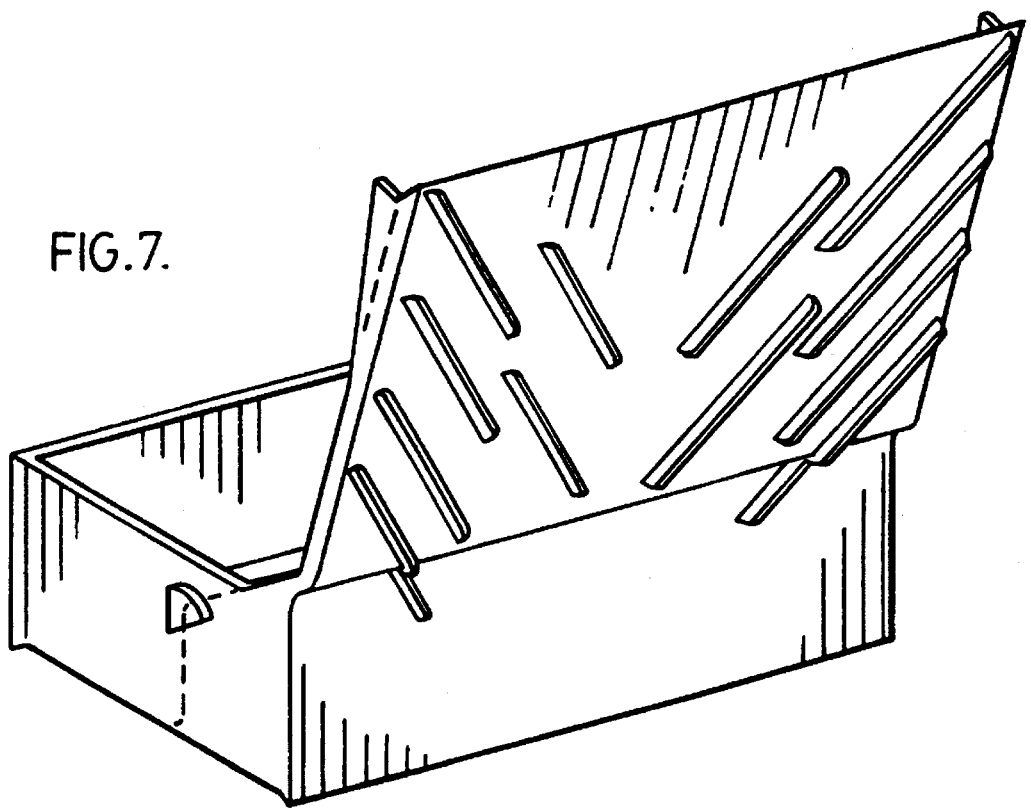
FIG. 7 is a rear perspective of a second embodiment of hopper.

The upper lip 65 of the front wall 64 of the hopper and bottom drip edge 69 prevents the initial sample of urine from flowing towards the channel 50. The outer surface 78 of the hopper rear wall 68 and upper portion of the housing rear wall 31 were not exposed to the initial stream of urine and therefore are relatively free of contaminants. Vanes 88 provided on the outer surface 78 of the rear wall 68 direct the urine towards the middle of the lower portion 26 of the housing and into the channel 50. Rather than using a pair of vanes as shown in FIG. 6, a plurality of vanes could be used to divert the flow as shown in FIG. 7.

The mid-stream sample passes through hole 44 into the nozzle 45 and into the container 48.

Thus the first portion of the urine stream is collected and a portion of it is discarded and the mid-stream sample is collected in container 48.

As shown in FIG. 3, while the hopper is in its second position, tabs 84 of the rear wall 68 of the hopper 22 rest against the inner surface of the front wall 29 of the housing. Upper edge 86 of rear wall 68 of the hopper does not touch the inner surface of the front wall 29 thereby preventing contaminated urine from the inner surface of the front wall 29 of the upper portion of the housing from flowing onto the outer surface 78 of the rear wall of the hopper 22. In another embodiment, spacers on the inside of front wall 29 of the housing could be used in place of tabs 84 to space the upper edge 86 of the rear wall 68 away from the front wall of the housing.

As the patient continues to urinate, the container 48 fills. The channel 50 may also fill and overflow into the base of the lower portion of the housing. This excess urine flows out through apertures 54 and 56 in the base 34 into the toilet or bedpan.

When the patient has finished urinating, the device is turned upside down and excess urine is discarded into the toilet or bedpan. Nozzle 45 prevents all the urine from pouring out of container 48. The device is then turned upright and the container 48 is removed, capped and stored for future urinalysis. The device is then discarded or collected for recycling.

Figure 5:
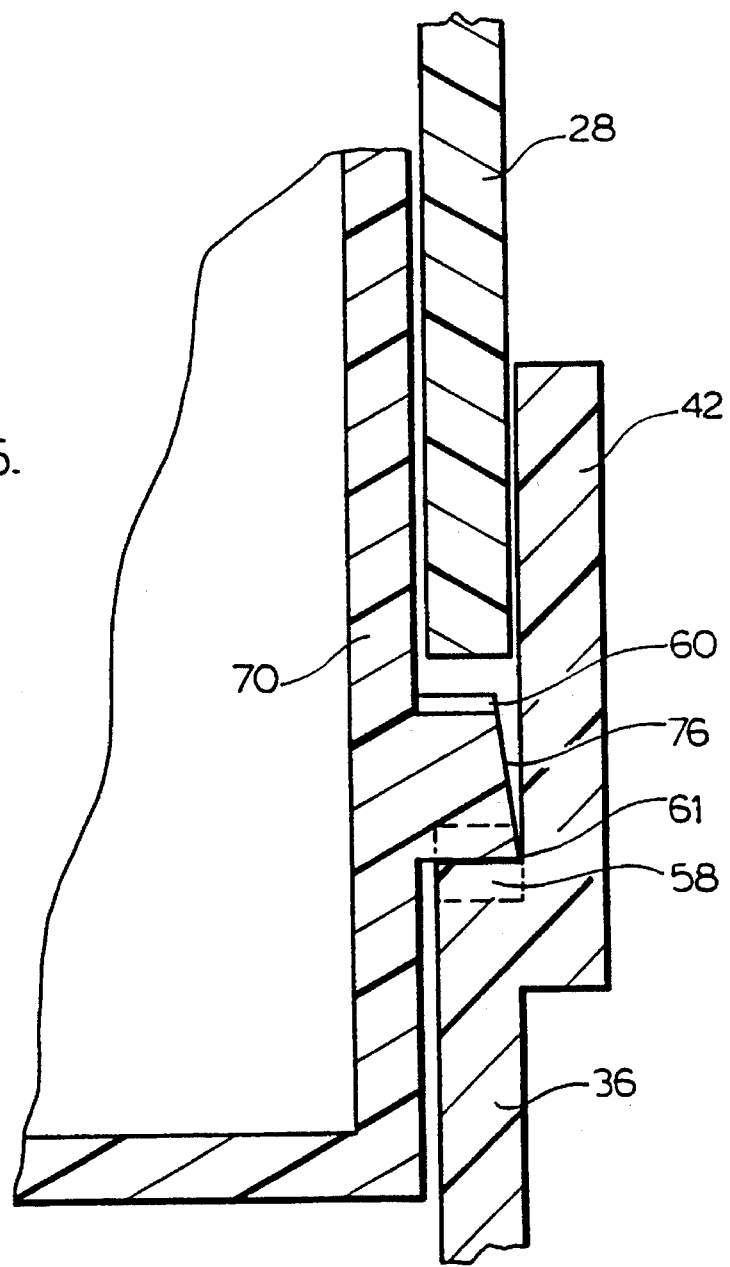
FIG. 5 is a section on the line 5—5 of FIG. 3.

Friction between the end walls 70 of the hopper and the periphery walls of the upper and lower portions of the housing is reduced by avoiding contact between them. As shown in FIG. 5, the knife edge 60 touches the upstanding flange 42 thereby spacing the end walls 70 of the hopper away from the periphery walls 28 and 36 of the housing and notches 58. Reducing the size of tip 61 of the knife edge reduces the friction.

Other variations and modifications of the invention are possible—for example, the device could be used to discard the first sample of the stream of other fluids. The hopper could be an asymmetric funnel, so long as the rate of fluid flow entering the funnel exceeded the rate of fluid flow leaving the funnel. Instead of knife edges, a pin could be used to permit the hopper to roll from first to second positions.

All such modifications or variations are believed to be within the sphere and scope of the invention as defined by the claims in this patent.

The embodiments of the invention in which an exclusive property of privilege is claimed are defined as follows:

1. A fluid sample collection device comprising a housing having an inlet to receive a stream of fluid and an outlet connectible to a container to retain a mid-stream fluid sample, a hopper movably located in said housing and having a cavity to collect fluid flowing through said inlet, said hopper being adapted to move from a first position in which said cavity is orientated to collect from said inlet a predetermined volume of the first portion of the fluid stream and thereby inhibit flow between said inlet and said outlet to a second position in which at least a part of said predetermined volume of fluid is discarded and a surface of said hopper is impinged by the fluid stream and is directed to the outlet.

2. A device according to claim 1 wherein said housing has a second outlet and said part of said predetermined volume is discarded to said second outlet.

3. A device according to claim 2 wherein said hopper is pivotally mounted in said housing.

4. A device according to claim 3 wherein said cavity is formed as an elongate trough having a pair of oppositely disposed end walls and arms are located on said end walls to cooperate with said housing to define pivot connections between said hopper and said housing.

5. The device according to claim 4 wherein said arms are formed as a knife edge.

6. The device according to claim 5 wherein the housing is provided with fulcrum blocks adapted to receive said knife edges.

7. The device according to claim 6 wherein each of said arms tapers to a point adjacent an inner wall of the housing thereby maintaining the end wall of the hopper in spaced relationship from the housing.

8. The device according to claim 4 wherein said elongate trough is disposed substantially to one side of said pivot connections.

9. The device according to claim 8 wherein said hopper includes a rear wall extending upwardly from said trough.

10. The device according to claim 9 wherein said rear wall has an outwardly directed surface defining said impingement surface when said hopper is in said second position.

11. The device according to claim 10 wherein said outwardly directed surface of said hopper is provided with vanes to direct the flow of fluid towards said outlet.

12. The device according to claim 10 wherein an upper edge of said rear wall of the hopper abuts a back wall of the housing when said hopper is in said first position.

13. The device according to claim 12 wherein said housing includes a front wall opposite to said back wall and said rear wall includes spacers to abut said front wall and maintain said upper edge spaced from said front wall when said hopper is in said second position.

14. The device according to claim 13 wherein said housing has a base extending between said front and back walls and said outlets are provided in said base.

15. The device according to claim 14 wherein said housing is provided with a channel defined by baffles extending upwardly from said base about said outlet to direct the fluid impinging on said outwardly directed surface of said rear wall of the hopper into said outlet when said hopper is in said second position.

16. The device according to claim 13 wherein said second outlet includes at least one aperture disposed in said base and outside of said channel to permit the predetermined volume of urine and excess urine from the mid-stream to exit from the housing.

17. The device according to claim 16 wherein said channel is disposed adjacent said back wall and rearwardly of said elongate trough and movement of said hopper to said second position discharges said part of said predetermined volume forwardly toward said front wall of said hopper.

18. The device according to claim 3 wherein said housing includes a pair of end walls longitudinally spaced with a front wall, back wall and base extending therebetween and said cavity includes an elongate trough pivotally mounted on said side walls for movement between said first and second positions.

19. The device according to claim 18 wherein said trough includes a front wall and a rear wall and said rear wall of said trough extends upwardly beyond said front wall of said trough.

20. The device according to claim 19 wherein said hopper is configured when in said first position to have its centre of mass rearwardly of said pivot connection when empty and forwardly of said pivot connection when said predetermined volume of fluid is collected.

21. The device according to claim 19 wherein said rear wall has an outwardly directed surface defining said impingement surface when said hopper is in said second position.

22. The device according to claim 21 wherein said outwardly directed surface of said hopper is provided with vanes to direct the flow of urine towards said outlet.

23. The device according to claim 21 wherein an upper edge of said rear wall of the hopper abuts a back wall of the housing when said hopper is in said first position.

24. The device according to claim 23 wherein said housing includes a front wall opposite to said back wall and said rear wall includes spacers to maintain said upper edge of said rear wall of said hopper spaced from said front wall of said housing when said hopper is in said second position.

25. The device according to claim 24 wherein said outlets are provided in said base.

26. The device according to claim 25 wherein said housing is provided with a channel defined by baffles extending upwardly from said base about said outlet to direct the urine impinging on said outwardly directed surface of said rear wall of the hopper into said outlet when said hopper is in said second position.

27. The device according to claim 26 wherein said second outlet includes at least one aperture disposed in said base and outside of said channel to permit the predetermined volume of urine and excess urine from the mid-stream to exit from the housing.

28. The device according to claim 27 wherein said channel is disposed adjacent said back wall and rearwardly of said elongate trough and movement of said hopper to said second position discharges said predetermined volume forwardly toward said front wall.

29. The device according to claim 4 wherein said housing is comprised of upper and lower portions joined at the equator of the housing by the upper portion being retained by a ledge and an upstanding wall provided in the lower portion.

30. The device according to claim 29 wherein said arems are supported by said ledge.

31. The device according to claim 30 wherein said ledge includes a pair of notches to receive respective ones of said arms.

32. The device according to claim 31 wherein each of said arms is formed as a knife edge and said notches receive said knife edges to define said pivot connection.

33. The device according to claim 32 wherein each of said arms tapers to a point adjacent to said upstanding wall.

34. The device according to claim 33 wherein a lower edge of said upper portion is relieved at opposite locations to accomodate said arms.

35. The device according to claim 29 wherein said upper portion has an end wall with facets extending upwardly and inwardly to said inlet.

36. A method of collecting a sample from a midportion flowing urine stream with a housing having an inlet and an outlet connected to a container for retaining the sample, the housing including a hopper having a cavity positioned to collect urine in the stream flowing through the inlet, as well as a surface positioned to direct fluid in the stream incident thereon to the outlet, the method comprising:

positioning the housing so the hopper is at a first location while an initial portion of the stream prior to the sample is flowing, the first location being such that the cavity is oriented to collect the initial stream portion flowing through the inlet so a predetermined volume of the initial portion is collected in the hopper and is prevented from reaching the outlet moving the hopper to a second position, and while the hopper is at the second position, discharging at least a portion of the collected sample while permitting the midstream sample to be incident on the surface, the mid-stream sample incident on the surface flowing from the surface to the container via the outlet.

* * * * *